(12) United States Patent
Degaspari et al.

(10) Patent No.: US 9,271,448 B2
(45) Date of Patent: Mar. 1, 2016

(54) METHOD FOR CULTIVATING SUGAR CANE

(75) Inventors: Nilton Degaspari, Piracicaba (BR); Antonio Cesar Azenha, Ribeirao Preto (BR); Paulo Cesar Queiroz, Valinhos (BR); Cassio da Silva Cardoso Teixeira, Sao Paulo (BR); Frank Werner, Sao Paulo (BR); Marco Antonio Tavares-Rodrigues, Sao Paulo (BR)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/702,369

(22) PCT Filed: Jun. 8, 2011

(86) PCT No.: PCT/EP2011/059419
§ 371 (c)(1),
(2), (4) Date: Dec. 6, 2012

(87) PCT Pub. No.: WO2011/154419
PCT Pub. Date: Dec. 15, 2011

(65) Prior Publication Data
US 2013/0074404 A1 Mar. 28, 2013

Related U.S. Application Data

(60) Provisional application No. 61/352,843, filed on Jun. 9, 2010.

(30) Foreign Application Priority Data

Jun. 9, 2010 (EP) ..................... 10165425
Apr. 15, 2011 (EP) ..................... 11162687

(51) Int. Cl.
A01N 43/56 (2006.01)
A01G 1/00 (2006.01)
A01N 25/00 (2006.01)
A01N 47/24 (2006.01)

(52) U.S. Cl.
CPC ................ *A01G 1/001* (2013.01); *A01N 25/00* (2013.01); *A01N 47/24* (2013.01)

(58) Field of Classification Search
CPC ............................... A01N 43/56; A01N 47/50
See application file for complete search history.

(56) References Cited

U.S. PATENT DOCUMENTS

| 4,091,569 | A | 5/1978 | Da Silva |
| 5,981,554 | A | 11/1999 | Bull et al. |
| 6,482,425 | B1 | 11/2002 | Huet et al. |
| 2008/0261811 | A1 | 10/2008 | Krohn et al. |
| 2008/0274882 | A1 | 11/2008 | Krohn et al. |

FOREIGN PATENT DOCUMENTS

| CH | 702011 | 4/2011 |
| CN | 1265268 | 9/2000 |
| CN | 101133738 | 3/2008 |
| EP | 0 295 117 | 12/1988 |
| EP | 0 882 746 | 10/1996 |
| EP | 1 066 854 | 1/2001 |
| EP | 2 005 812 | 12/2008 |
| GB | 926856 | 5/1963 |
| JP | 8 280244 | 10/1996 |
| JP | 10 324605 | 12/1998 |
| JP | 2000 135025 | 5/2000 |
| JP | 2003 204716 | 7/2003 |
| WO | WP 2012/140177 | 10/1820 |
| WO | WO 86/06576 | 11/1986 |
| WO | WO 91/14356 | 10/1991 |
| WO | WO 98/11780 | 3/1998 |
| WO | WO 02/076178 | 10/2002 |
| WO | WO 2008/043471 | 4/2008 |
| WO | WO 2008/059053 | 5/2008 |
| WO | WO 2008/059054 | 5/2008 |
| WO | WO 2008/095913 | 8/2008 |
| WO | WO 2008095913 | * 8/2008 |
| WO | WO 2009/000398 | 12/2008 |
| WO | WO 2009/000399 | 12/2008 |
| WO | WO 2009/000400 | 12/2008 |
| WO | WO 2009/000401 | 12/2008 |
| WO | WO 2009/000402 | 12/2008 |
| WO | WO 2009/024546 | 2/2009 |
| WO | WO 2009/100916 | 8/2009 |

(Continued)

OTHER PUBLICATIONS

International Search Report dated Sep. 8, 2011, prepared in International Application No. PCT?Ep2011/059419, filed Jun. 8, 2011.
Office Action dated Aug. 7, 2014 from U.S. Appl. No. 13/805,546.
Final Office Action dated Jan. 13, 2015 from U.S. Appl. No. 13/805,546.
Grossmann et al., "Bioregulatory Effects of the Fungicidal Strobilurin Kresoxim-methyl in Wheat (*Triticum aestivum*)", Pesticide Science, 1997, vol. 50, No. 1, pp. 11-20.
Jabs et al., "Anti-oxidative and anti-senescence effects of the strobilurin pyraclostrobin in plants: A new strategy to cope with environmental stress in cereals", The BCPC Conference—Pests & Diseases, 2002, pp. 941-946.

(Continued)

*Primary Examiner* — Alton Pryor
(74) *Attorney, Agent, or Firm* — Brinks Gilson & Lione

(57) ABSTRACT

The present invention relates to a method for cultivating sugar cane comprising planting sugar cane shoots in a growth medium, growing seedlings from the shoots at a temperature of at least 15° C. and 10-120 days after having planted the shoots planting the seedlings obtained therefrom into the field if the growth medium is not a field, or, in case the growth medium is a field, exposing the seedlings obtained from the shoots to ambient conditions, where the seedling, while growing, is treated with at least one strobilurin fungicide and/or at least one carboxamide fungicide and/or at least one GABA antagonist insecticide and/or at least one nicotinic receptor agonists/antagonist insecticide and/or at least one chloride channel activator insecticide.

28 Claims, No Drawings

(56) References Cited

FOREIGN PATENT DOCUMENTS

| WO | WO 2009/100917 | | 8/2009 |
|---|---|---|---|
| WO | WO 2011161071 | * | 6/2011 |
| WO | WO 2011/154419 | | 12/2011 |
| WO | WO 2011/161071 | | 12/2011 |
| WO | WO 2012/140177 | | 10/2012 |
| WO | WO 2013/041665 | | 3/2013 |
| WO | WO 2013/160241 | | 10/2013 |
| WO | WO 2013/160242 | | 10/2013 |

OTHER PUBLICATIONS

Nason et al., "Strobilurin fungicides induce changes in photosynthetic gas exchange that do not improve water use efficiency of plants grown under conditions of water stress", Pest Management Science, 2007, vol. 63, pp. 1191-1200.

Nitzan et al., "Effect of Seed-Tuber Generation, Soilborne Inoculum, and Azoxystrobin Application on Development of Potato Black Dot Caused by *Colletotrichum coccodes*", Plant Disease, Nov. 2005, pp. 1181-1185.

Venancio et al., "Physiological Effects of Strobilurin Fungicides on Plants", Publ. UEPG Exact Soil Sci. Agr. Sci. Eng., Ponta Grossa, 2003, vol. 9, No. 3, pp. 59-68.

Bartlett et al., "The strobilurin fungicides", Pest Management Science, 2002, vol. 58, No. 7, pp. 649-662.

Grossman et al., "Bioregulatory Effects of the Fungicidal Strobilurin Kresoxim-methyl in Wheat (*Triticum aestivurn*)", Pesticide Science, 1997, vol. 50, No. 1, pp. 11-20.

Jabs et al., "Anti-oxidative and anti-senescence effects of the strobilurin pyraclostrobin in plants: A new strategy to cope with environment stress in cerals", The BCPC Conference—Pests & Diseases, 2002, pp. 941-946.

Nason et al., "Strobilurin fungicides induce changes in photosynthetic gas exchange that do not improve water use effciency of plants grown under conditions of water stress", Pest Management Science, 2007, vol. 63, pp. 1191-1200.

Nitzan et al., "Effect of Seed-Tuber Generation, Sallborne Inoculum, and Azoxystrobin Application on Development of Potato Black Dot Caused by *Colletoricham coccodes*", Plant Disease, Nov. 2005, pp. 1181-1185.

Sugar Cane: technical aspects about forty-five agricultural crops in Costa Rica: General Directorate of Agricultural Research and Extension, Ministry of Agriculture and Livestock, San Jose, Costa Rica, 1991.

Venancio et al. "Physiological Effects of Strobilurin Fungicides on Plants", Publ, UEPG Exact Soil Sci. Agr. Sci. Eng. Ponta Grossa, 2003, vol. 9, No. 3, pp. 59-68.

International Preliminary Report on Patentability issued Dec. 10, 2012, prepared in International Application No. PCT/EP2011/059419, filed Jun. 8, 2011.

\* cited by examiner

METHOD FOR CULTIVATING SUGAR CANE

This application is a National Stage application of International Application No. PCT/EP2011/059419, filed Jun. 8, 2011, which claims the benefit of U.S. Provisional Application No. 61/352,843 filed Jun. 9, 2010, the entire contents of which are hereby incorporated herein by reference. This application also claims priority under 35 U.S.C. §119 to European Patent Application No. 10165425.9 filed Jun. 9, 2010, and European Patent Application No. 11162687.5, filed Apr. 15, 2011, the entire contents of which is hereby incorporated herein by reference.

The present invention relates to a method for cultivating sugar cane comprising planting sugar cane shoots in a growth medium, growing seedlings from the shoots at a temperature of at least 15° C. and 10-120 days after having planted the shoots planting the seedlings obtained therefrom into the field if the growth medium is not a field, or, in case the growth medium is a field, exposing the seedlings obtained from the shoots to ambient conditions, where the seedling, while growing, is treated with at least one strobilurin fungicide and/or at least one carboxamide fungicide and/or at least one GABA antagonist insecticide and/or at least one nicotinic receptor agonists/antagonist insecticide and/or at least one chloride channel activator insecticide.

Taking into account the finiteness of fossil fuel supply, biofuels have been rediscovered as an important energy source. Sugar cane is one of the plants which are yet used for the production of biofuels (bioethanol) and is promising for further development, as the alcohol obtained by the fermentation of these plants provides a renewable and clean fuel. The plantation area of sugar cane is increasing worldwide as well as the investments in factories to produce alcohol therefrom.

The seed of sugar cane is a dry one-seeded fruit or caryopsis formed from a single carpel, the ovary wall (pericarp) being united with the seed-coat (testa). The seeds are ovate, yellowish brown and very small, about 1 mm long. Disadvantageously, the seed of sugar cane only germinates under specific environmental characteristics, such as a constant warm and humid climate conditions. Such climatic conditions are not found everywhere sugar cane is grown, and therefore germination of sugar cane seed is not always guaranteed. For commercial agriculture, the seed of a sugar cane is not sown or planted, but instead, the cane is propagated vegetatively by planting a stem segment (or part of a stalk or culm or seedling). As mentioned above, the stem of sugar cane, as well as the stem of graminaceous plants, comprises several nodes, from which new plants grow. The traditional planting process of sugar cane involves the reservation of an area of the crop to be used as a source of plants for replanting, since the nodes are comprised in the stem. The plants used for replanting are harvested and then cut in segments of approximately 20-50 cm so that at least 2 nodes are present in each stem segment (sett). Cutting the stems is needed to break apical dominance that otherwise causes poor germination when using full length (uncut) stems. The segments are cut to have at least 2 buds (or at least two nodes; every node gives generally rise to one single bud) to assure germination, because not every bud germinates. Current machines used to cut sugar cane segments are not able to identify any characteristic in the stem, and therefore the precise position of the cut sites is determined at random.

After cutting, the setts are disposed horizontally, over one another in furrows of the ploughed soil, which are generally wide at ground level and deep (40 to 50 cm wide and 30 to 40 cm deep), and then lightly covered with soil.

Although this plantation technique is still being used until today, the whole process is relatively inefficient, because many segments of 2-4 nodes have to be used to guarantee the germination. The consequence is that a large area for re-planting needs to be used, and therefore area that could be employed for the crop and production of alcohol or sugar has to be reserved for re-planting. Thus, there is a necessity to increase the efficiency of the planting technique of sugar cane.

In a more recent cultivation method from Syngenta (called Plene®), nodes of less than 4 cm in length are separated from the stems, treated with Syngenta seed products and then planted to the field. The method is said to lead to a yield increase of up to 15%. However, the area required for multiplication is still very large. Similar cultivation methods are also described in WO 2009/000398, WO 2009/000399, WO 2009/000400, WO 2009/000401 and WO 2009/000402.

JP 08-280244 describes a method for producing sugar cane seedlings by germinating buds from lateral buds of sugar cane, growing these buds, removing the head parts of the grown buds, whereby new buds germinate from the lateral buds of the cut buds, and repeating this process steps once or several times. This process is said to allow mass production of sugar cane seedlings. A similar method is described in JP 2003-204716 and JP 2000-135025.

It was therefore an object of the present invention to provide a method for cultivating sugar cane which requires a small area for multiplication and yields healthier and resistant plants.

The object is achieved by a method (method A) for cultivating sugar cane, which method comprises planting a shoot of a sugar cane plant in a growth medium;
optionally treating the shoot and/or the growth medium before, during or shortly after planting with at least one fertilizer and/or at least one fungicide and/or at least one insecticide and/or at least one nematicide and/or at least one growth regulator and/or at least one superabsorber and/or growth-promoting bacteria;
growing a seedling from the shoot at a temperature of at least 15° C.;
treating the seedling, while growing, with at least one strobilurin fungicide and/or at least one carboxamide fungicide and/or at least one GABA antagonist insecticide and/or at least one nicotinic receptor agonists/antagonist insecticide and/or at least one chloride channel activator insecticide and optionally also with at least one fungicide different therefrom and/or at least one insecticide different therefrom and/or at least one nematicide and/or at least one growth regulator and/or at least one rooting enabler and/or growth-promoting bacteria;
10 to 120 days after planting the shoots in the growth medium, if the growth medium is not a field, planting the seedling obtained from the shoots to the field, where the field has optionally been treated with at least one fertilizer and/or at least one fungicide and/or at least one insecticide and/or at least one nematicide and/or at least one growth regulator and/or at least one superabsorber and/or growth-promoting bacteria before or during planting, or, in case the growth medium is a field, exposing the seedlings obtained from the shoots to ambient conditions; and
optionally treating the seedlings and/or the field during or after planting in the field or after exposing to ambient conditions with least one fungicide and/or at least one insecticide and/or at least one nematicide and/or at least one growth regulator and/or at least one superabsorber and/or at least one freshness-preservation polymer.

In the terms of the present invention, "stem" is the caulis or stalk of the culm part of a graminaceus plant (here: the sugar cane plant), i.e. the main trunk of a plant, specifically a primary plant axis that develops buds and shoots.

"Sett" is a stem segment, section or cutting having one or more nodes.

"Node" is the location in the stem where the shoot, bud or gemma is formed in a graminaceus plant (here: the sugar cane plant).

"Shoot", "bud" or "gemma" is the embryo, spore or germ of a graminaceus plant (here: the sugar cane plant).

"Germinate"/"germination" is the emergence of a new plant from a shoot/bud.

"Seedling" is the young plant emerging/sprouting from a shoot/bud. Within the terms of the present invention, the young plants are called "seedlings" starting from germination/sprouting until planting to a field (if the shoot is first grown in a growth medium which is not a field) or until the young plant is exposed to ambient conditions (if the shoot is directly planted to a field).

The following remarks made to preferred embodiments of the features of the method of the invention apply both alone as well as in particular in combination with each other.

In a preferred embodiment of the invention, the sugar cane shoot is obtained in following steps:
(i) breaking in a living 6 to 18 months old sugar cane plant the apical dominance by cutting off the top part of the stalk so that the below stalk still comprises 5 to 15 nodes, and/or by treating the plant or a part thereof with an herbicide, and/or by a method different therefrom;
(ii) in case that the apical dominance is broken by cutting off the top part of the stalk: optionally treating the cut surface of the below stalk obtained in step (i) with at least one fungicide and/or at least one insecticide and/or at least one wound-protecting material and/or at least one growth regulator;
(iii) cutting off the top part of at least some of the shoots emerged from the nodes of the below stalk obtained in steps (i) or (ii) above the meristematic tissue;
(iv) optionally treating the cut surface of the shoots obtained in step (iii) with at least one fungicide and/or at least one insecticide and/or at least one wound-protecting material and/or at least one growth regulator;
(v) optionally cutting off the top part of the newly formed shoots emerged from the cut shoots obtained in steps (iii) or (iv) above the meristematic tissue;
(vi) optionally treating the cut surface of the shoots obtained in step (v) with at least one fungicide and/or at least one insecticide and/or at least one wound-protecting material and/or at least one growth regulator;
(vii) optionally repeating step (v) and optionally also step (vi) one or several times;
(viii) cutting off the newly formed shoots emerged from the cut shoots obtained in steps (iii), (iv), (v), (vi) or (vii) when they are 10 to 60 cm long so that they comprise at least part of the meristematic tissue,
and using these for planting in said growth medium.

Thus, preferably, the method of the invention comprises following steps:
(i) breaking in a living 6 to 18 months old sugar cane plant the apical dominance by cutting off the top part of the stalk so that the below stalk still comprises 5 to 15 nodes, and/or by treating the plant or a part thereof with an herbicide, and/or by a method different therefrom;
(ii) in case that the apical dominance is broken by cutting off the top part of the stalk: optionally treating the cut surface of the below stalk obtained in step (i) with at least one fungicide and/or at least one insecticide and/or at least one wound-protecting material and/or at least one growth regulator;
(iii) cutting off the top part of at least some of the shoots emerged from the nodes of the below stalk obtained in steps (i) or (ii) above the meristematic tissue;
(iv) optionally treating the cut surface of the shoots obtained in step (iii) with at least one fungicide and/or at least one insecticide and/or at least one wound-protecting material and/or at least one growth regulator;
(v) optionally cutting off the top part of the newly formed shoots emerged from the cut shoots obtained in steps (iii) or (iv) above the meristematic tissue;
(vi) optionally treating the cut surface of the shoots obtained in step (v) with at least one fungicide and/or at least one insecticide and/or at least one wound-protecting material and/or at least one growth regulator;
(vii) optionally repeating step (v) and optionally also step (vi) one or several times;
(viii) cutting off the newly formed shoots emerged from the cut shoots obtained in steps (iii), (iv), (v), (vi) or (vii) when they are 10 to 60 cm long so that they comprise at least part of the meristematic tissue;
(ix) optionally treating the shoots obtained in step (viii) with at least one fungicide and/or at least one insecticide and/or at least one nematicide and/or at least one wound-protecting material and/or at least one growth regulator;
(x) planting the shoots obtained in step (viii) or (ix) in a growth medium;
(xi) optionally treating the shoots and/or the growth medium before, during or shortly after planting with at least one fertilizer and/or at least one fungicide and/or at least one insecticide and/or at least one nematicide and/or at least one growth regulator and/or at least one superabsorber and/or growth-promoting bacteria;
(xii) growing seedlings from the shoots at a temperature of at least 15° C.;
(xiii) treating the seedlings, while growing, and/or their growth medium with at least one strobilurin fungicide and/or at least one carboxamide fungicide and/or at least one GABA antagonist insecticide and/or at least one nicotinic receptor agonists/antagonist insecticide and/or at least one chloride channel activator insecticide and optionally also with at least one fungicide different therefrom and/or at least one insecticide different therefrom and/or at least one nematicide and/or at least one growth regulator and/or at least one rooting enabler and/or growth-promoting bacteria;
(xiv) 10 to 120 days after planting the shoots in the growth medium, if the growth medium is not a field, planting the seedlings obtained from the shoots to the field, where the field has optionally been treated with at least one fertilizer and/or at least one fungicide and/or at least one insecticide and/or at least one nematicide and/or at least one growth regulator and/or at least one superabsorber and/or growth-promoting bacteria before or during planting, or, in case the growth medium is a field, exposing the seedlings obtained from the shoots to ambient conditions; and
(xv) optionally treating the seedlings and/or the field during or after planting in the field or after exposing to ambient conditions with at least one fertilizer and/or at least one fungicide and/or at least one insecticide and/or at least one nematicide and/or at least one growth regulator and/or at least one superabsorber and/or growth-promoting bacteria and/or at least one freshness-preservation polymer.

The remarks made below with respect to steps (i) to (xv) apply to the corresponding steps of the above method A, too.

"Apical dominance" is a phenomenon in plant physiology whereby the main central stem of the plant is dominant over side stems. The apical bud produces the growth hormone auxin, which diffuses downward and inhibits the development of lateral bud growth, which otherwise would compete with the apical tip. Interrupting the auxin flux and thus breaking the apical dominance allows the lower dormant lateral buds to develop.

By breaking the apical dominance in step (i), the emergence of lateral shoots from the nodes on the below, remaining plant is induced. As a rule, each productive node produces on average one shoot. Of course, there are unproductive nodes and productive nodes producing more than one shoot, but most productive nodes give rise to one shoot. Removing a part of these shoots in step (iii) triggers the production of more than one lateral shoot per node (or, more precisely per remainder of the first, original shoot). As a rule, each productive node produces on average three shoots. Here again, there are unproductive nodes and nodes producing less than three shoots or nodes producing more than three shoots, but most nodes give rise to three shoots. In sum, in step (viii), as an average, 3 to 6 times more shoots are removed than there are in step (iii), depending on whether steps (v) and (vii) are carried out or not. Thus, in the method of the invention each sugar cane plant used in step (i) gives rise to an average of 10 to 12 seedlings, which is in average three times the number obtained in conventional planting.

Step (i) is preferably carried out when the sugar cane plant is 8 to 12 months old.

In a preferred embodiment, the apical dominance is broken in step (i) by cutting off the top part of the stalk so that the below, remaining stalk still comprises about 5 to 15, preferably 8 to 15 and in particular 8 to 12 nodes.

"Cutting off" refers in the context of the present invention to any suitable procedure for removing the top part, such as cutting, chopping or sawing, e.g. with a knife, machete, axe, saw or any suitable machine, or by breaking off or tearing off manually the top part.

The removal of the top part of the plant can be carried out manually or automatedly.

Specifically, in step (i) the removed top part of the plant comprises the last, top node or, in other words, the top part is removed in such a way that the below, remaining stalk doesn't comprise the top node any more.

In another embodiment, the apical dominance is broken in step (i) by treating the plant or a part thereof with an herbicide.

Suitable herbicides are those that break apical dominance, e.g. herbicide with an anti-auxin activity.

Examples are h1) inhibitors of acetyl CoA carboxylase, such as FOPs, e.g. clodinafop propargyl, cyhalofop butyl, diclofop methyl, fenoxaprop-P-ethyl, fluazifop-P-butyl, haloxyfop-R-methyl, propaquizafop and quizalofop-P-ethyl; and DIMs, e.g. alloxydim, butroxydim, clethodim, cycloxydim, profoxydim, sethoxydim, tepraloxydim, tralkoxydim, h2) herbicides which interact with photosystem I electron diversion, such as bipyridilium compounds, e.g. diquat and parquet;

h3) auxin transport inhibitors, such as diflufenzopyr, diflufenzopyr-sodium, naptalam and naptalam-sodium.

Among the inhibitors of acetyl CoA carboxylase, preference is given to the FOPs. Among the FOPs, preference is given to fluazifop-P-butyl.

Among the herbicides which interact with photosystem I electron diversion, preference is given to paraquat.

Among the auxin transport inhibitors, preference is given to diflufenzopyr and diflufenzopyr-sodium.

Preferably, inhibitors of acetyl CoA carboxylase are used, more preferably the FOPs and specifically fluazifop-P-butyl.

The suitable application rates of the herbicides depend on the specific herbicide used. For fluazifop-P-butyl a preferred application rate is 12-75 g/ha.

Approximately 5 to 30 days after the treatment the top part of the plant begins to die off. When this process reaches the region of the top node, step (iii) is initiated.

The apical dominance can also be broken by means different from cutting off the top part or herbicidal treatment. Such means include hormonal treatments with "anti-auxins", such as cytokinins, for example adenine cytokinins, e.g. benzyladenin and kinetin; or diphenylurea cytokinins.

Preferably, apical dominance is broken by cutting off the top part of the plant.

In optional step (ii), if apical dominance has been broken by cutting off the top part of the plant, the cut surface of the below stalk obtained in step (i) is treated with at least one fungicide and/or at least one insecticide and/or at least one wound-protecting material and/or at least one growth regulator.

In terms of the present invention, the term "cut surface" is not restricted to a surface obtained by specifically cutting off a plant part, but refers to any open surface obtained by any means for removing said plant part.

This treatment is carried out for protecting this "open wound" from diseases and pests, but also for supporting physiological effects. Suitable and preferred fungicides, insecticides, wound-protecting materials and growth regulators are listed below. Among the fungicides, especial preference is given to the treatment with fungicides which also have a physiological, especially a plant health and/or growth-promoting effect, such as the strobilurins and especially pyraclostrobin. Preferred is the treatment with at least one fungicide, in particular a strobilurin fungicide, especially pyraclostrobin, and/or at least one growth regulator.

Preferably, step (ii) is carried out.

After development of shoots step (iii) is carried out. Preferably step (iii) is carried out when the emerged shoots are preferably from 10 to 60 cm, more preferably from 25 to 30 cm long and contain at least one node.

In step (iii) the top part of at least some of the shoots emerged from the nodes of the stalk pieces (to be more precise from the buds on the nodes) is cut off above the meristematic tissue, so that the cut-off pieces do not contain any meristem. Thus they cannot survive as they cannot develop any roots and are generally discarded. The meristematic tissue is known to those skilled in the art and can be located by its position close to the node. However the cut-off pieces contain at least the top node of the shoot.

Here too, "cutting off" refers to any suitable procedure for removing the top part, such as cutting, chopping or sawing, e.g. with a knife, machete, axe, saw or any suitable machine, or by breaking off or tearing off manually the top part.

The removal is preferably carried out manually, for instance by breaking, tearing, cutting or chopping off.

In optional step (iv) the cut surface obtained in step (iii) where the top part of the shoots has been removed is treated with at least one fungicide and/or at least one insecticide and/or at least one wound-protecting material and/or at least one growth regulator. This treatment is carried out for protecting this "open wound" from diseases and pests, but also for supporting physiological effects. Suitable and preferred fungicides, insecticides, wound-protecting materials and growth regulators are listed below. Among the fungicides, especial preference is given to the treatment with fungicides which also have a physiological, especially a plant health and/or growth-promoting effect, such as the strobilurins and especially pyraclostrobin. Preferred is the treatment with at least one fungicide, in particular a strobilurin fungicide, especially pyraclostrobin, and/or at least one growth regulator.

As already mentioned, removing the top part of the shoots in step (iii) induces the production of new shoots—this time in an enhanced number as compared to the number obtained directly after the removal of the top part of the sugar cane plant.

These newly emerged shoots can either be used for planting (via steps (viii) et seq.; see below), or they can be subjected to optional steps (v) and (vi), which represents a repetition of steps (iii) and (iv). For steps (v) and (vi) the same remarks made for steps (iv) and (v) apply.

In optional step (vii), steps (v) and optionally (vi) can be repeated once or several times. Steps (v) and (vi) can principally be repeated endlessly, but the number of repetitions is in often limited by the quality of the newly emerged shoots, which diminishes with every repetition, and generally doesn't exceed 5 times.

Preferably, steps (v) and optionally (vi) are carried out at most once (or in other words: repetition step (vii) is preferably not carried out). Specifically, steps (vi) and (vii) are not carried out, which means that the new shoots obtained after steps (iii) or (iv) are directly subjected to step (viii).

In step (viii) the newly formed shoots emerged from the cut shoots obtained in steps (iii), (iv), (v), (vi) or (vii) are cut off when they are 10 to 60 cm long. They are cut off in such a way that they comprise at least part of the meristem. The presence of meristematic tissue enables the cut-off shoots to produce roots and grow. For this purpose the shoots are removed close to the node from which they originate.

The new shoots are preferably cut off when they are 10 to 40 cm long, more preferably 20 to 40 cm long and in particular 25 to 30 cm long.

Here too, "cutting off" refers to any suitable procedure for removing or detaching the shoots, such as cutting, chopping or sawing, e.g. with a knife, machete, axe, saw or any suitable machine, or by breaking off or tearing off manually the shoots.

The removal is preferably carried out manually, for instance by breaking, tearing, cutting or chopping off.

In optional step (ix) the shoots obtained in step (viii) are treated with at least one fungicide and/or at least one insecticide and/or at least one nematicide and/or at least one wound-protecting material and/or at least one growth regulator. This treatment is carried out for protecting the "open wound" of the cut-off shoots from diseases and pests, but especially for supporting physiological effects. Suitable and preferred fungicides, insecticides, nematicides, wound-protecting material and growth regulators are listed below. Among the fungicides, especial preference is given to the treatment with fungicides which also have a physiological, especially a plant health and/or growth-promoting effect, such as the strobilurins and especially pyraclostrobin. Preferred is the treatment with at least one fungicide, in particular a strobilurin fungicide, especially pyraclostrobin, and/or at least one growth regulator.

These shoots obtained in steps (viii) or (ix) are then planted in a growth medium [step (x)].

The growth medium may be a natural or synthetic substrate or a mixture thereof. Examples are soil, clay, sand, silt, small wood chops, cellulose, decayed organic residues, vermiculite, coconut fibers and the like and mixtures thereof. Among these, preference is given to preferably soil, vermiculite or coconut fibers, specifically coconut fibers. The growth medium may also be a nutrient solution, such as an aqueous solution containing growth factors, fertilizers, buffers, ion exchangers, inorganic salts, such as calcium salts (e.g. calcium nitrate, calcium sulphate, calcium hydrogen phosphate), magnesium salts (e.g. magnesium nitrate, magnesium sulphate), potassium salts (e.g. potassium dihydrogen phosphate, potassium nitrate), iron salts (e.g. ferrous sulfate, ferric chloride) and micronutrients (e.g. lithium salts, such as lithium chloride, copper salts, such as copper sulfate, zinc salts, such as zinc sulfate, aluminium salts, such as aluminium sulfate, nickel salts, such as nickel sulfate, tin salts, such as tin chloride, cobalt salts, such as cobalt nitrate, boric acid) and mixtures thereof like Knop's nutrition solution and Hoagland's A-Z solution, and the like. The nutrient solution may be form-stabilized, e.g. by an inorganic substrate, such as expanded clay. Moreover, the growth medium may be the soil in a field.

In optional step (xi) the growth medium may be treated before, during and/or after planting the shoots with at least one fertilizer and/or at least one fungicide and/or at least one insecticide and/or at least one nematicide and/or at least one growth regulator and/or at least one superabsorber and/or growth-promoting bacteria. Suitable and preferred fertilizers, fungicides, insecticides, nematicides, growth regulators, superabsorbers and growth-promoting bacteria are described below. Among the fungicides, especial preference is given to the treatment with fungicides which also have a physiological, especially a plant health and/or growth-promoting effect, such as the strobilurins and especially pyraclostrobin. Preferred is the treatment with at least one fungicide, in particular a strobilurin fungicide, especially pyraclostrobin, and/or at least one growth regulator.

Alternatively or additionally, the shoot may be treated before and/or during planting with at least one fungicide and/or at least one insecticide and/or at least one nematicide and/or at least one growth regulator. Suitable and preferred fungicides, insecticides, nematicides and growth regulators are described below. Among the fungicides, especial preference is given to the treatment with fungicides which also have a physiological, especially a plant health and/or growth-promoting, e.g. a rooting enabling effect, such as the strobilurins and especially pyraclostrobin. Preferred is the treatment with at least one fungicide, in particular a strobilurin fungicide, especially pyraclostrobin, and/or at least one growth regulator.

In a preferred embodiment step (xi) is carried out. Preferably the shoot and/or the growth medium are treated with at least one strobilurin fungicide and optionally also with at least one fungicide different therefrom and/or at least one fertilizer and/or at least one insecticide and/or at least one nematicide and/or at least one growth regulator and/or at least one superabsorber and/or growth-promoting bacteria. Suitable and preferred strobilurin fungicides are listed below. Specific preference is given to pyraclostrobin.

In a preferred embodiment, in step (x), the shoots are planted in a container containing a growth medium. Suitable growth media are listed above. Preferred growth media to be used in a container are selected from soil, clay, sand, silt, small wood chops, cellulose, decayed organic residues, vermiculite, coconut fibers and the like and mixtures thereof and are more preferably soil, vermiculite or coconut fibers, specifically coconut fibers.

The container may be made of a conventional material or a biodegradable material. Biodegradable containers have the advantage that the seedling can be planted together with the container into the field, i.e. there is no need to remove the seedling from the container before planting. This in turn has the advantage that planting can be carried out using an automatic or semi-automatic planting machine.

In a specific embodiment, a biodegradable container is used in step (x). The biodegradable container is based on a biodegradable material which in turn is preferably based on biodegradable polyesters, starch, cellulose, cellulosic material, polylactic acid, caoutchouc, paper, paperboard, pulp of cellulosic origin, straw, bagasse, sawdust, natural fibres or mixtures thereof.

In an alternative specific embodiment, the container is a conventional (i.e. not specifically biodegradable) one.

After planting the shoots into the growth medium and optionally after the treatment of the shoots and/or the growth medium with at least one fertilizer, at least one fungicide, at least one insecticide, at least one nematicide, at least one growth regulator, at least one superabsorber and/or growth-promoting bacteria, seedlings are grown from the shoots at a temperature of at least 15° C. Preferably, seedlings are grown from the shoots at a temperature of from 15 to 35° C., more preferably from 18 to 35° C., even more preferably from 20 to 35° C., in particular from 22 to 35° C., e.g. 22 to 30° C. or 22 to 28° C., and especially from 25 to 35° C., e.g. 25 to 30° C. or 25 to 28° C. or 25 to 27° C.

Preferably, seedlings are grown from the shoots at a humidity of from 40 to 100%, more preferably from 50 to 95%, even more preferably from 70 to 90% and in particular from 70 to 80%.

The required temperature is realized either naturally, for instance if the seedlings are grown from the shoots in a warm climate, e.g. in a tropical climate, or by the aid of artificial means. Artificial means are for example greenhouses or covering materials. The growing medium may for example be in a greenhouse or be transferred thereto after planting, or the growing medium containing the shoot may be thermally insulated, e.g. by covering with a suitable material, such as a foil.

In one preferred embodiment, the shoots are planted into a container containing a growth medium, where the container is in a greenhouse or is placed into a greenhouse after planting.

In the greenhouse, the temperature is preferably in the range of from 15 to 35° C., more preferably from 18 to 35° C., even more preferably from 20 to 35° C., in particular from 22 to 35° C., e.g. 22 to 30° C. or 22 to 28° C., and especially from 25 to 35° C., e.g. 25 to 30° C. or 25 to 28° C. or 25 to 27° C. Humidity is preferably in the range of from 40 to 100%, more preferably from 50 to 95%, even more preferably from 70 to 90% and in particular from 70 to 80%.

In an alternatively preferred embodiment, the shoots are planted into a container containing a growth medium or into a field (in this case the growth medium is the soil of the field) and the container or the field is covered with one or more covering materials.

Covering materials are for example textile mats and cover foils customarily used for thermal insulation/protection in agriculture, such as agriculture plastic foil, preferably black foil, for example in the form of foil tunnels, or fleece mats.

In step (xiii) the seedlings, while growing at a temperature of at least 15° C., and/or their growth medium are treated once or several times, e.g. 1, 2 or 3 times, preferably once or twice, with at least one strobilurin fungicide and/or at least one carboxamide fungicide and/or at least one GABA antagonist insecticide and/or at least one nicotinic receptor agonists/antagonist insecticide and/or at least one chloride channel activator insecticide and optionally also with a further fungicide different therefrom and/or at least one insecticide different therefrom and/or at least one nematicide and/or at least one growth regulator and/or at least one rooting enabler and/or growth-promoting bacteria. Suitable and preferred fungicides different from strobilurins and carboxamide fungicides, insecticides different from GABA antagonists, nicotinic receptor agonists/antagonists and chloride channel activators, nematicides, growth regulators, rooting enablers and growth-promoting bacteria are described below. Treating the seedling means in this context that either the seedling or the growth medium or both are treated. If treatments with at least one fungicide different from strobilurins, at least one insecticide and/or at least one nematicide are carried out depends among others on the (type and intensity of) pest pressure.

Preferably, the at least one strobilurin fungicide (i.e. the strobilurin used in step (xiii) or preferably used in the optional treatment steps) is selected from azoxystrobin, dimoxystrobin, enestroburin, fluoxastrobin, kresoxim-methyl, metominostrobin, orysastrobin, picoxystrobin, pyraclostrobin, pyraoxystrobin, pyrametostrobin, pyribencarb, trifloxystrobin, 2-(2-(6-(3-chloro-2-methyl-phenoxy)-5-fluoro-pyrimidin-4-yloxy)-phenyl)-2-methoxyimino-N-methyl-acetamide, 3-methoxy-2-(2-(N-(4-methoxy-phenyl)-cyclopropane-carboximidoylsulfanylmethyl)-phenyl)-acrylic acid methyl ester, methyl (2-chloro-5-[1-(3-methylbenzyloxyimino)ethyl]benzyl)carbamate and 2-(2-(3-(2,6-dichlorophenyl)-1-methyl-allylideneaminooxymethyl)-phenyl)-2-methoxyimino-N-methyl-acetamide. More preferred strobilurin fungicides are selected from azoxystrobin, dimoxystrobin, fluoxastrobin, fluxapyroxade, kresoxim-methyl, orysastrobin, picoxystrobin, pyraclostrobin and trifloxystrobin. Specifically, the strobilurin fungicide is pyraclostrobin.

The at least one strobilurin fungicide is preferably used in an application rate of from 1 to 500 g/ha, more preferably from 10 to 200 g/ha and in particular from 50 to 150 g/ha.

Preferably, the at least one carboxamide fungicide [i.e. the carboxamide fungicide used in step (xiii)] is selected from benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penthiopyrad, sedaxane, tecloftalam, thifluzamide, tiadinil, 2-amino-4-methyl-thiazole-5-carboxanilide, 2-chloro-N-(1,1,3-trimethyl-indan-4-yl)-nicotinamide, N-(3',4',5'-tri-fluorobiphenyl-2-yl)-3-difluoromethyl-1-methyl-1H-pyrazole-4-carboxamide (fluxapyroxad), N-(4'-trifluoromethylthiobiphenyl-2-yl)-3-difluoromethyl-1-methyl-1H-pyrazole-4-carboxamide, N-(2-(1,3-dimethyl-butyl)-phenyl)-1,3-dimethyl-5-fluoro-1H-pyrazole-4-carboxamide and N-(2-(1,3,3-trimethyl-butyl)-phenyl)-1,3-dimethyl-5-fluoro-1H-pyrazole-4-carboxamide, dimethomorph, flumorph, pyrimorph, flumetover, fluopicolide, fluopyram, zoxamide, N-(3-ethyl-3,5,5-trimethyl-cyclohexyl)-3-formylamino-2-hydroxy-benzamide, carpropamid, dicyclomet, mandiproamid, oxytetracyclin, silthiofam and N-(6-methoxy-pyridin-3-yl)cyclopropanecarboxylic acid amide. More preferably, it is selected from boscalid and fluxapyroxad.

Preferably, the at least one GABA antagonist [i.e. the GABA antagonist insecticide used in step (xiii)] is selected from acetoprole, endosulfan, vaniliprole, pyrafluprole, pyriprole, the phenylpyrazole compound of the formula II

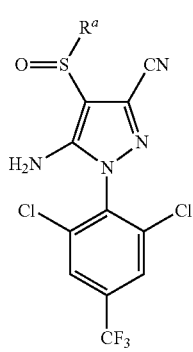

where $R^a$ is $C_1$-$C_4$-alkyl or $C_1$-$C_4$-haloalkyl;
or an agriculturally acceptable salt thereof;
and the phenylpyrazole compound of the formula III

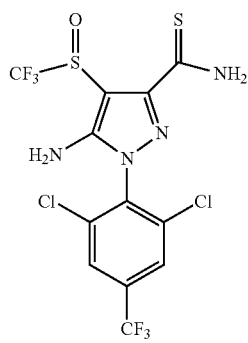

or an agriculturally acceptable salt thereof.

Moreover, the GABA antagonist insecticide is selected from fipronil.

Preferably, the at least one nicotinic receptor agonists/antagonist insecticide [i.e. the nicotinic receptor agonists/antagonist insecticide used in step (xiii)] is selected from acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022. More preferably, the at least one nicotinic receptor agonists/antagonist insecticide is selected from acetamiprid, clothianidin, imidacloprid and thiamethoxam.

Preferably, the at least one chloride channel activator insecticide [i.e. the nicotinic receptor agonists/antagonist insecticide used in step (xiii)] is selected from abamectin, emamectin, ivermectin, lepimectin and milbemectin. More preferably, the at least one chloride channel activator insecticide is abamectin.

In one preferred embodiment, the seedlings, while growing, and/or their growth medium [i.e. in step (xiii)] are treated with at least one strobilurin fungicide.

In an alternatively preferred embodiment, the seedlings, while growing, and/or their growth medium [i.e. in step (xiii)] are treated with at least one carboxamide fungicide.

In an alternatively preferred embodiment, the seedlings, while growing, and/or their growth medium [i.e. in step (xiii)] are treated with at least one GABA antagonist insecticide.

In an alternatively preferred embodiment, the seedlings, while growing, and/or their growth medium [i.e. in step (xiii)] are treated with al least one nicotinic receptor agonists/antagonist insecticide.

In an alternatively preferred embodiment, the seedlings, while growing, and/or their growth medium [i.e. in step (xiii)] are treated with at least one chloride channel activator insecticide.

In an alternatively preferred embodiment, the seedlings, while growing, and/or their growth medium [i.e. in step (xiii)] are treated with at least one strobilurin fungicide and at least one GABA antagonist insecticide.

Among the fungicides and insecticides to be mandatorily used while the seedling is growing, i.e. in step (xiii), more preference is given to the strobilurin fungicides and GABA antagonist insecticides. Suitable and preferred strobilurin fungicides and GABA antagonist insecticides are listed above. Specific preference is given to pyraclostrobin and fipronil. Even more preference is given to the strobilurin fungicides and especially to pyraclostrobin.

10 to 120, preferably 25 to 100 days after having planted the shoot in the growth medium, the seedling which has grown from the shoot is planted to the field (of course only if the growth medium is not yet a field). At this point of time, the seedling has generally a length of from 20 to 80 cm. Planting to the field is more preferably carried out 25 to 80 days, even more preferably 40 to 70 days, in particular 50 to 70 days and specifically 60±5 days after having planted the shoot in the growth medium.

In a preferred embodiment, the seedlings, before being planted to the field are allowed to acclimatize, i.e. they are allowed to adapt to conditions as they are present in the field. For this purpose they can for example be brought into an area with weather conditions similar or identical to the conditions in the field, i.e. with changes in temperature, humidity, rain, drought etc, or the roof of the glass house can be partially or completely removed. This acclimatization is generally carried out 3 weeks to 1 day, preferably 3 weeks to one week before planting to the field.

Before, during or shortly after planting to the field or shortly after exposing to ambient conditions the seedlings are optionally pruned.

The field has optionally been treated with at least one fertilizer and/or at least one fungicide and/or at least one insecticide and/or at least one nematicide and/or at least one growth regulator and/or at least one superabsorber and/or growth-promoting bacteria before planting. These treatments can also be carried out during planting, for instance in the form of an in-furrow application. Suitable and preferred fertilizers, fungicides, insecticides, nematicides, growth regulators, superabsorbers and growth-promoting bacteria are described below.

If the field is the growth medium, 10 to 120, preferably 25 to 100, more preferably 25 to 80 days, even more preferably 40 to 70 days, in particular 50 to 70 days and specifically 60±5 days after having planted the shoot, the seedling grown therefrom is exposed to ambient conditions, i.e. is no longer protected thermally. For instance, if the thermal protection has been realized by means of a covering material, such as a cover foil or a fleece mat, this is removed.

During or after planting in the field or after exposing to ambient conditions, the seedling or the field may be treated with at least one fertilizer and/or at least one fungicide and/or at least one insecticide and/or at least one nematicide and/or at least one growth regulator and/or at least one superabsorber and/or growth-promoting bacteria and/or at least one freshness-preservation polymer. Suitable and preferred fertilizers, fungicides, insecticides, nematicides, growth regulators, superabsorbers, growth-promoting bacteria and freshness-preservation polymers are described below.

Planting into the field may take place manually, semi-automatically or automatedly. Planting can for example take place totally automatedly if biodegradable containers are used for planting the shoots and growing the seedlings therein. In this case, the seedlings needn't be taken out of the containers before planting, which allows the use of a planting machine for the whole process of planting. In case a conventional container is used, the seedlings have to be taken out the container before planting, which is generally carried out manually. Planting can then take place automatedly.

In the above treatments, the at least one fungicide is preferably selected from

A) azoles, selected from the group consisting of
  azaconazole, bitertanol, bromuconazole, cyproconazole, difenoconazole, diniconazole, diniconazole-M, epoxiconazole, etaconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-(4-chloro-phenyl)-2-([1,2,4]triazol-1-yl)-cycloheptanol, cyazofamid, imazalil, pefurazoate, prochloraz, triflumizol, benomyl, carbendazim, fuberidazole, thiabendazole, ethaboxam, etridiazole, hymexazole and 2-(4-chloro-phenyl)-N-[4-(3,4-dimethoxy-phenyl)-isoxazol-5-yl]-2-prop-2-ynyloxy-acetamide;

B) strobilurins, selected from the group consisting of
  azoxystrobin, dimoxystrobin, enestroburin, fluoxastrobin, kresoxim-methyl, meto-minostrobin, orysastrobin, picoxystrobin, pyraclostrobin, pyraoxystrobin, pyrametostrobin, pyribencarb, trifloxystrobin, 2-(2-(6-(3-chloro-2-methyl-phenoxy)-5-fluoro-pyrimidin-4-yloxy)-phenyl)-2-methoxyimino-N-methyl-acetamide, 3-methoxy-2-(2-(N-(4-methoxy-phenyl)-cyclopropane-carboximidoylsulfanylmethyl)-phenyl)-acrylic acid methyl ester, methyl (2-chloro-5-[1-(3-methylbenzyloxyimino)-ethyl]benzyl)carbamate and 2-(2-(3-(2,6-dichlorophenyl)-1-methyl-allylidene-aminooxymethyl)-phenyl)-2-methoxyimino-N-methyl-acetamide;

C) carboxamides, selected from the group consisting of
  benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penthiopyrad, sedaxane, tecloftalam, thifluzamide, tiadinil, 2-amino-4-methyl-thiazole-5-carboxanilide, 2-chloro-N-(1,1,3-trimethyl-indan-4-yl)-nicotinamide, N-(3',4',5'-trifluorobiphenyl-2-yl)-3-difluoromethyl-1-methyl-1H-pyrazole-4-carboxamide (fluxapyroxade), N-(4'-trifluoromethylthiobiphenyl-2-yl)-3-difluoromethyl-1-methyl-1H-pyrazole-4-carboxamide, N-(2-(1,3-dimethyl-butyl)-phenyl)-1,3-dimethyl-5-fluoro-1H-pyrazole-4-carboxamide and N-(2-(1,3,3-trimethyl-butyl)-phenyl)-1,3-dimethyl-5-fluoro-1H-pyrazole-4-carboxamide, dimethomorph, flumorph, pyrimorph, flumetover, fluopicolide, fluopyram, zoxamide, N-(3-ethyl-3,5,5-trimethyl-cyclohexyl)-3-formylamino-2-hydroxy-benzamide, carpropamid, dicyclomet, mandiproamid, oxytetracyclin, silthiofam and N-(6-methoxy-pyridin-3-yl)cyclopropanecarboxylic acid amide;

D) heterocyclic compounds, selected from the group consisting of
  fluazinam, pyrifenox, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine, 2,3,5,6-tetra-chloro-4-methanesulfonyl-pyridine, 3,4,5-trichloropyridine-2,6-di-carbonitrile, N-(1-(5-bromo-3-chloro-pyridin-2-yl)-ethyl)-2,4-dichloronicotinamide, N-[(5-bromo-3-chloro-pyridin-2-yl)-methyl]-2,4-dichloro-nicotinamide, bupirimate, cyprodinil, diflumetorim, fenarimol, ferimzone, mepanipyrim, nitrapyrin, nuarimol, pyrimethanil, triforine, fenpiclonil, fludioxonil, aldimorph, dodemorph, dodemorph-acetate, fenpropimorph, tridemorph, fenpropidin, fluoroimid, iprodione, chlozolinate, procymidone, vinclozolin, famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester, acibenzolar-S-methyl, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole, 5-chloro-7-(4-methylpiperidin-1-yl)-6-(2,4,6-trifluorophenyl)-[1,2,4]triazolo[1,5-a]pyrimidine and 5-ethyl-6-octyl-[1,2,4]triazolo[1,5-a]pyrimidine-7-ylamine;

E) carbamates, selected from the group consisting of
  ferbam, mancozeb, maneb, metam, methasulphocarb, metiram, propineb, thiram, zineb, ziram, benthiavalicarb, pyributicarb, diethofencarb, iprovalicarb, iodocarb, propamocarb, propamocarb hydrochlorid, prothiocarb, valiphenal and N-(1-(1-(4-cyano-phenyl) ethanesulfonyl)-but-2-yl) carbamic acid-(4-fluorophenyl) ester;

F) other active compounds, selected from the group consisting of
  guanidines: guanidine, dodine, dodine free base, guazatine, guazatine-acetate, iminoctadine, iminoctadine-triacetate, iminoctadine-tris(albesilate);
  antibiotics: kasugamycin, kasugamycin hydrochloride-hydrate, streptomycin, polyoxine, validamycin A;
  nitrophenyl derivates: binapacryl, dinobuton, dinocap, meptyldinocap, nitrthal-isopropyl, tecnazen,
  organometal compounds: fentin salts, such as fentin-acetate, fentin chloride or fentin hydroxide;
  sulfur-containing heterocyclyl compounds: dithianon, isoprothiolane;
  organophosphorus compounds: edifenphos, fosetyl, fosetyl-aluminum, iprobenfos, phosphorous acid and its salts, pyrazophos, tolclofos-methyl;
  organochlorine compounds: chlorothalonil, dichlofluanid, dichlorophen, flusulfamide, hexachlorobenzene, pencycuron, pentachlorphenole and its salts, phthalide, quintozene, thiophanate-methyl, tolylfluanid, N-(4-chloro-2-nitro-phenyl)-N-ethyl-4-methyl-benzenesulfonamide;
  inorganic active substances: Bordeaux mixture, copper acetate, copper hydroxide, copper oxychloride, basic copper sulfate, sulfur;
  others: biphenyl, bronopol, cyflufenamid, chloroneb, cymoxanil, dicloran, tecnazene, diphenylamin, metrafenone, mildiomycin, oxin-copper, prohexadione-calcium, spiroxamine, tolylfluanid, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5- trifluoromethyl-4-(3-trimethylsilanyl-propoxy)-phenyl)-N-ethyl-N-methyl formamidine, N'-(5-difluoromethyl-2-methyl-4-(3-tri-methylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, acetic acid 6-tert.-butyl-8-fluoro-2,3-dimethyl-quinolin-4-yl ester and methoxy-acetic acid 6-tert-butyl-8-fluoro-2,3-dimethyl-quinolin-4-yl ester;
and G) biological control agents.

Biological control is defined as the reduction of pest population by natural enemies and typically involves an active human role. The biological control of plant diseases is most often based on an antagonistic action of the BCA. There are several mechanisms by which fungicidal biocontrol is thought to work, including the production of antifungal antibiotics, competition for nutrients and rhizosphere colonization.

Suitable biological control agents are selected from non-pathogenic bacteria, preferably selected from *Pseudomonas fluorescens, Pseudomonas putida. Streptomyces griseus, Streptomyces ochraceisleroticus, Streptomyces graminofaciens, Streptomyces corchousii, Streptomyces spiroverticillatus, Streptomyces griseoviridis, Streptomyces hygroscopicus, Bacillus subtilis, Bacillus cereus, Bacillus mycoides, Bacillus pumilus, Bacillus licheniformis, Bacillus thuringensis*, and metabolites produced from said bacteria; non-pathogenic fungi, preferably selected from *Trichoderma* spp., *Trichoderma harzianum, Trichoderma viridae, Verticillium lecanii, Sporidesmium sclerotiorum* and Zygomycetes, and metabolites produced from said fungi; resin acids; plant extracts of *Reynoutria sachalinensis*; and plant defence induction agents, preferably harpin.

More preferably, the at least one fungicide is selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, cyazofamid, benomyl, carbendazim, ethaboxam, azoxystrobin, dimoxystrobin, fluoxastrobin, fluxapyroxade, kresoxim-methyl, orysastrobin, picoxystrobin, pyraclostrobin, trifloxystrobin, bixafen, boscalid, sedaxane, fenhexamid, metalaxyl, isopyrazam, mefenoxam, ofurace, dimethomorph, flumorph, fluopicolid (picobenzamid), zoxamide, carpropamid, mandipropamid, fluazinam, cyprodinil, fenarimol, mepanipyrim, pyrimethanil, triforine, fludioxonil, dodemorph, fenpropimorph, tridemorph, fenpropidin, iprodione, vinclozolin, famoxadone, fenamidone, probenazole, proquinazid, acibenzolar-S-methyl, captafol, folpet, fenoxanil, quinoxyfen, 5-ethyl-6-octyl-[1,2,4]triazolo[1,5-a]pyrimidine-7-ylamine, mancozeb, metiram, propineb, thiram, iprovalicarb, flubenthiavalicarb (benthiavalicarb), propamocarb, dithianon, fentin salts, fosetyl, fosetyl-aluminium, $H_3PO_3$ and salts thereof, chlorthalonil, dichlofluanid, thiophanat-methyl, copper acetate, copper hydroxide, copper oxychloride, copper sulfate, sulfur, cymoxanil, metrafenone, spiroxamine and *Bacillus subtilis* and its metabolites.

In particular, the at least one fungicide is a strobilurin fungicide or is *Bacillus subtilis* and/or its metabolites or is a combination of at least two of these fungicides. Preferred strobilurins are selected from azoxystrobin, dimoxystrobin, fluoxastrobin, fluxapyroxade, kresoxim-methyl, orysastrobin, picoxystrobin, pyraclostrobin and trifloxystrobin. Specifically, the strobilurin fungicide is pyraclostrobin.

In step (xiii), where the seedling is mandatorily treated with at least one strobilurin fungicide, the optional further fungicide is preferably selected from groups A) and C) to G). More preferably, the at least one fungicide is selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, cyazofamid, benomyl, carbendazim, ethaboxam, bixafen, boscalid, sedaxane, fenhexamid, metalaxyl, isopyrazam, mefenoxam, ofurace, dimethomorph, flumorph, fluopicolid (picobenzamid), zoxamide, carpropamid, mandipropamid, fluazinam, cyprodinil, fenarimol, mepanipyrim, pyrimethanil, triforine, fludioxonil, dodemorph, fenpropimorph, tridemorph, fenpropidin, iprodione, vinclozolin, famoxadone, fenamidone, probenazole, proquinazid, acibenzolar-S-methyl, captafol, folpet, fenoxanil, quinoxyfen, 5-ethyl-6-octyl-[1,2,4]triazolo[1,5-a]pyrimidine-7-ylamine, mancozeb, metiram, propineb, thiram, iprovalicarb, flubenthiavalicarb (benthiavalicarb), propamocarb, dithianon, fentin salts, fosetyl, fosetyl-aluminium, $H_3PO_3$ and salts thereof, chlorthalonil, dichlofluanid, thiophanat-methyl, copper acetate, copper hydroxide, copper oxychloride, copper sulfate, sulfur, cymoxanil, metrafenone, spiroxamine and *Bacillus subtilis* and its metabolites.

In the above treatments, the at least one insecticide is preferably selected from
a) pyrethroid compounds selected from acrinathrin, allethrin, d-cis-trans allethrin, d-trans allethrin, bifenthrin, bioallethrin, bioallethrin S-cyclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin and transfluthrin;
b) nicotinic receptor agonists/antagonists compounds selected from acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022;
c) GABA gated chloride channel antagonist compounds selected from chlordane, endosulfan, gamma-HCH (lindane); ethiprole, fipronil, pyrafluprole and pyriprole;
d) chloride channel activators selected from abamectin, emamectin benzoate, milbemectin and lepimectin; and
e) inhibitors of chitin biosynthesis:
  e1) benzoyl ureas: bistrifluoron, chlorfluazuron, diflubenzuron, flucycloxuron, flufenoxuron, hexaflumuron, lufenuron, novaluron, noviflumuron, teflubenzuron, triflumuron.

More preferably, the at least one insecticide is selected from fipronil, acetamiprid, chlothianidin, imidacloprid, thiamethoxam, abamectin and teflubenzuron, and is specifically fipronil.

In the above treatments, the at least one nematicide is preferably selected from
  antibiotic nematicides, such as abamectin;
  botanical nematicides, such as carvacrol;
  extracts of *Quillaja* or *Gleditsia*;

saponines;

carbamate nematicides selected from benomyl, carbofuran, carbosulfan and cloethocarb;

oxime carbamate nematicides selected from alanycarb, aldicarb, aldoxycarb, oxamyl and tirpate;

fumigant nematicides selected from dithioether and methyl bromide;

organophosphorus nematicides:
- organophosphate nematicides selected from diamidafos; fenamiphos; fosthietan and phosphamidon;
- organothiophosphate nematicides selected from cadusafos, chlorpyrifos, dichlofenthion, dimethoate, ethoprophos, fensulfothion, fosthiazate, heterophos, isamidofos, isazofos, phorate, phosphocarb, terbufos, thionazin and triazophos;
- phosphonothioate nematicides selected from imicyafos and mecarphon; and
- unclassified nematicides selected from acetoprole, benclothiaz, chloropicrin, dazomet, DBCP, DCIP, 1,2-dichloropropane, 1,3-dichloropropene, fluensulfone, furfural, metam, methyl iodide, methyl isothiocyanate and xylenols.

Specifically, the at least one nematicide is abamectin.

In the above treatments, the growth-promoting bacteria are preferably selected from bacteria of the genera *azospirillum, azotobacter, azomonas, bacillus, beijerinckia, burkholderia, clostridium, cyanobacteria, enterobacter, erwinia, gluconobacter, klebsiella* and *streptomyces*.

More preferably, the growth-promoting bacteria are selected from *Azospirillum amazonense, Herbaspirillum seropedicae, Herbaspirillum rubrisubalbicans, Burkholderia tropica, Gluconacetobacter diazotrophicus, Pseudomonas fluorescens, Pseudomonas putida. Streptomyces griseus, Streptomyces ochraceisleroticus, Streptomyces graminofaciens, Streptomyces corchousii, Streptomyces spiroverticillatus, Streptomyces griseoviridis, Streptomyces hygroscopicus, Bacillus subtilis, Bacillus cereus, Bacillus mycoides, Bacillus pumilus, Bacillus licheniformis* and *Bacillus thuringensis*.

In the above treatments, the at least one growth regulator is preferably selected from acylcyclohexanediones, such as prohexadione, prohexaione-Ca, trinexapac or trinexapac ethyl; mepiquat chloride and chlormequatchloride. More preferably, the at least one growth regulator is selected from acylcyclohexanediones, such as prohexadione, prohexaidone-Ca, trinexapac or trinexapac ethyl, and in particular from prohexaidone-Ca and trinexapac ethyl.

The at least one rooting enabler is preferably selected from the above strobilurin fungicides, in particular fluxapyroxade and pyraclostrobin, the above nicotinic receptor agonists/antagonists, in particular clothianidin, imidacloprid and thiamethoxam, auxins, such as 4-CPA, 2,4-D, 2,4-DB, 2,4-DEP, dichlorprop, fenoprop, IAA, IBA, naphthaleneacetamide, α-naphthaleneacetic acid, 1-naphthol, naphthoxyacetic acids, potassium naphthenate, sodium naphthenate and 2,4, 5-T; gibberellins, gibberellic acid, cytokinins, such as 2iP, benzyladenine, 4-hydroxyphenethyl alcohol, kinetin and zeatin; and humic acids, extracts of *Quillaja* or *Gleditsia*, saponines, biological control agents and plant defence induction agents.

Suitable fertilizers are those customarily used in the cultivation of sugar cane plants, such as NPK fertilizers, ammonium sulfate, ammonium phosphate, ammonium nitrate, ureas, products of vegetable origin, such as cereal meal, tree bark meal, wood meal, nutshell meal and mulch, and mixtures thereof.

The at least one superabsorber is preferably a superabsorbent polymer having an absorption capacity for deionised water of least 100 g/1 g of polymer. Superabsorbent polymers are well-known synthetic organic polymers which are solid and hydrophilic, which are insoluble in water, and which are capable of absorbing a multiple of their weight of water or aqueous solutions, thereby forming a water containing polymer gel. They may be nonionic or ionic crosslinked polymers. Suitable superabsorbent polymers are for example known from U.S. Pat. No. 4,417,992, U.S. Pat. No. 3,669,103, WO 01/25493 and WO 2008/031870. They are also commercially available, e.g. from SNF SA., France, under the trademark Aquasorb®, e.g. 3500 S, or from BASF SE under the trade names Luquasorb®, e.g. Luquasorb® 1010, Luquasorb® 1280, Luquasorb® 1060, Luquasorb® 1160, Luquasorb® 1061 and HySorb®.

The wound-protecting material is preferably selected from non-toxic inorganic and organic film-forming or coating polymers, such as superabsorbers, superabsorber-treated polymers (e.g. Luquafleece® from BASF) aliphatic-aromatic copolyesters (e.g. Ecoflex® from BASF), freshness-preservation polymers (e.g. FreshSeal® from BASF), waxes, soluble glass and naturally occurring swelling substances (e.g. Tingui (Magonia pubescens) seed coat preparations, especially powder from the seed coat of Tingui or to be more precise gel formed from said powder). Among these, preference is given to FreshSeal® and gel prepared from pulverized seed coat of Tingui.

The fungicides, insecticides, nematicides, growth regulators and rooting enablers are generally used as ready-to-use preparations. In the following, suitable ready-to-use preparations containing at least one fungicide, insecticide, nematicide, growth regulator or rooting enabler (called in the following "active ingredient") are described.

In ready-to-use preparations, the active ingredient can be present in suspended, emulsified or dissolved form. The application forms depend entirely on the intended uses.

The active ingredient can be applied as such, in the form of its formulations or the application form prepared therefrom, for example in the form of directly sprayable solutions, powders, suspensions or dispersions, including highly concentrated aqueous, oily or other suspensions or dispersions, emulsions, oil dispersions, pastes, dusts, compositions for broadcasting or granules. Application is usually by spraying, atomizing, dusting, broadcasting or watering. The application forms and methods depend on the intended uses; in each case, they should ensure the finest possible distribution of the active compounds.

Depending on the embodiment in which the ready-to-use preparations of the active ingredient is present, they comprise one or more liquid or solid carriers, if appropriate surfactants and if appropriate further auxiliaries customary for formulating crop protection agents. The recipes for such formulations are familiar to the person skilled in the art.

Aqueous application forms can be prepared, for example, from emulsion concentrates, suspensions, pastes, wettable powders or water-dispersible granules by addition of water. To prepare emulsions, pastes or oil dispersions, the active compounds, as such or dissolved in an oil or solvent, can be homogenized in water by means of a wetting agent, tackifier, dispersant or emulsifier. However, it is also possible to prepare concentrates composed of active substance, wetting agent, tackifier, dispersant or emulsifier and, if appropriate, solvent or oil, such concentrates being suitable for dilution with water.

The concentrations of the active ingredient in the ready-to-use preparations can be varied within relatively wide ranges. In general, they are between 0.0001 and 10%, preferably between 0.01 and 1% (% by weight total content of active compound, based on the total weight of the ready-to-use preparation).

The active ingredient may also be used successfully in the ultra-low-volume process (ULV), it being possible to employ formulations comprising more than 95% by weight of active compound, or even to apply the active ingredient without additives.

Oils of various types, wetting agents, adjuvants, herbicides, bactericides and/or fertilizers may be added to the active ingredient, even, if appropriate, not until immediately prior to use (tank mix). These agents can be mixed in a weight ratio of from 1:100 bis 100:1, preferably from 1:10 to 10:1 with the active ingredient employed.

Adjuvants are for example: modified organic polysiloxanes, e.g. Break Thru S 240®; alcohol alkoxylates, e.g. Atplus 245®, Atplus MBA 1303®, Plurafac LF 300® and Lutensol ON 30®; EO-PO block copolymers, e.g. Pluronic RPE 2035® and Genapol B®; alcohol ethoxylates, e.g. Lutensol XP 80®; and sodium dioctylsulfosuccinate, e.g. Leophen RA®.

The formulations are prepared in a known manner, for example by extending the active ingredient with solvents and/or carriers, if desired with the use of surfactants, i.e. emulsifiers and dispersants. Solvents/carriers suitable for this purpose are essentially:

water, aromatic solvents (for example Solvesso products, xylene), paraffins (for example mineral oil fractions), alcohols (for example methanol, butanol, pentanol, benzyl alcohol), ketones (for example cyclohexanone, methyl hydroxybutyl ketone, diacetone alcohol, mesityl oxide, isophorone), lactones (for example gamma-butyrolactone), pyrrolidones (pyrrolidone, N-methylpyrrolidone, N-ethylpyrrolidone, n-octylpyrrolidone), acetates (glycol diacetate), glycols, dimethyl fatty acid amides, fatty acids and fatty acid esters. In principle, solvent mixtures may also be used.

Carriers such as ground natural minerals (for example kaolins, clays, talc, chalk) and ground synthetic minerals (for example finely divided silica, silicates); emulsifiers such as nonionic and anionic emulsifiers (for example polyoxyethylene fatty alcohol ethers, alkylsulfonates and arylsulfonates), and dispersants such as lignosulfite waste liquors and methylcellulose.

Suitable surfactants are alkali metal salts, alkaline earth metal salts and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenyl polyglycol ether, tributylphenyl polyglycol ether, tristerylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Suitable for the preparation of directly sprayable solutions, emulsions, pastes or oil dispersions are mineral oil fractions of medium to high boiling point, such as kerosene or diesel oil, furthermore coal tar oils and oils of vegetable and animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, mesityl oxide, isophorone, strongly polar solvents, for example dimethyl sulfoxide, 2-yrrolidone, N-methylpyrrolidone, butyrolactone, or water.

Powders, compositions for broadcasting and dusts can be prepared by mixing or jointly grinding the active ingredient with a solid carrier.

Granules, for example coated granules, impregnated granules and homogeneous granules, can be prepared by binding the active ingredient onto solid carriers. Solid carriers are, for example, mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers such as, for example, ammonium sulfate, ammonium phosphate, ammonium nitrate, ureas and plant products such as cereal meal, tree bark meal, wood meal and nutshell meal, cellulose powder and other solid carriers.

Formulations for shoot treatment can further comprise binders and/or gelling agents and optionally colorants.

In general, the formulations comprise between 0.01 and 95% by weight, preferably between 0.1 and 90% by weight, in particular 5 to 50% by weight, of the active ingredient. In this context, the active ingredient is employed in a purity of from 90% to 100%, preferably 95% to 100% (according to NMR spectrum).

After two- to ten-fold dilution, formulations for shoot treatment may comprise 0.01 to 60% by weight, preferably 0.1 to 40% by weight of the active ingredient in the ready-to-use preparations.

Examples of formulations are:
1. Products for Dilution in Water
I) Water-Soluble Concentrates (SL, LS)

10 parts by weight of active compound are dissolved in 90 parts by weight of water or a water-soluble solvent. Alternatively, wetting agents or other adjuvants are added. Upon dilution in water, the active compound dissolves. The ready formulation contains 10% by weight of active ingredient.

II) Dispersible Concentrates (DC)

20 parts by weight of active compound are dissolved in 70 parts by weight of cyclohexanone with addition of 10 parts by weight of a dispersant, for example polyvinylpyrrolidone. The active ingredient is contained in 20% by weight. Upon dilution in water, a dispersion results.

III) Emulsifiable Concentrates (EC)

15 parts by weight of active compound are dissolved in 75 parts by weight of xylene with addition of calcium dodecylbenzenesulfonate and castor oil ethoxylate (in each case 5 parts by weight). The active ingredient is contained in 15% by weight. Upon dilution in water, an emulsion results.

IV) Emulsions (EW, EO, ES)

25 parts by weight of active compound are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier (Ultraturrax) and made into a homogeneous emulsion. The active ingredient is contained in 25% by weight. Upon dilution in water, an emulsion results.

V) Suspensions (SC, OD, FS)

20 parts by weight of active compound are comminuted in a stirred ball mill with addition of 10 parts by weight of dispersants, wetting agents and 70 parts by weight of water or an organic solvent to give a fine suspension of active compound. The active ingredient is contained in 20% by weight. Upon dilution in water, a stable suspension of the active compound results.

VI) Water-Dispersible and Water-Soluble Granules (WG, SG)

50 parts by weight of active compound are ground finely with addition of 50 parts by weight of dispersants and wetting agents and made into water-dispersible or water-soluble granules by means of technical apparatuses (for example extrusion, spray tower, fluidized bed). The active ingredient is contained in 50% by weight. Upon dilution in water, a stable dispersion or solution of the active compound results.

VII) Water-Dispersible and Water-Soluble Powders (WP, SP, SS, WS)

75 parts by weight of active compound are ground in a rotor-stator mill with addition of 25 parts by weight of dispersants, wetting agents and silica gel. The active ingredient is contained in 75% by weight. Upon dilution in water, a stable dispersion or solution of the active compound results.

VIII) Gel Formulations (GF)

20 parts by weight of active compound, 10 parts by weight of dispersants, 1 part by weight of gelling agent and 70 parts by weight of water or an organic solvent are ground in a ball mill to give a finely divided suspension. Upon dilution in water, a stable suspension of the active compound results.

2. Products for Direct Application

IX) Dusts (DP, DS)

5 parts by weight of active compound are ground finely and mixed intimately with 95 parts by weight of finely particulate kaolin. This gives a dust with 5% by weight of active ingredient.

X) Granules (GR, FG, GG, MG)

0.5 part by weight of active compound is ground finely and combined with 95.5 parts by weight of carriers. Current methods are extrusion, spray drying or the fluidized bed. This gives granules for direct application with 0.5% by weight of active ingredient.

XI) ULV Solutions (UL)

10 parts by weight of active compound are dissolved in 90 parts by weight of an organic solvent, for example xylene. This gives a product for direct application with 10% by weight of active ingredient.

Formulations suitable for treating the shoots are, for example:
I soluble concentrates (SL, LS)
III emulsifiable concentrates (EC)
IV emulsions (EW, EO, ES)
V suspensions (SC, OD, FS)
VI water-dispersible and water-soluble granules (WG, SG)
VII water-dispersible and water-soluble powders (WP, SP, WS)
VIII gel formulations (GF)
IX dusts and dust-like powders (DP, DS)

Preferred formulations to be used for shoot treatment are FS formulations. Generally, theses formulations comprise 1 to 800 g/l of active compounds, 1 to 200 g/l of wetting agents, 0 to 200 g/l of antifreeze agents, 0 to 400 g/l of binders, 0 to 200 g/l of colorants (pigments and/or dyes) and solvents, preferably water.

Preferred FS formulations of the active compounds for the treatment of the shoots usually comprise from 0.5 to 80% of active compound, from 0.05 to 5% of wetting agent, from 0.5 to 15% of dispersant, from 0.1 to 5% of thickener, from 5 to 20% of antifreeze agent, from 0.1 to 2% of antifoam, from 0 to 15% of tackifier or adhesive, from 0 to 75% of filler/vehicle, and from 0.01 to 1% of preservative.

Suitable wetting agents and dispersants are in particular the surfactants mentioned above. Preferred wetting agents are alkylnaphthalenesulfonates, such as diisopropyl- or diisobutylnaphthalenesulfonates. Preferred dispersants are nonionic or anionic dispersants or mixtures of nonionic or anionic dispersants. Suitable nonionic dispersants are in particular ethylene oxide/propylene oxide block copolymers, alkylphenol polyglycol ethers and also tristryrylphenol polyglycol ether, for example polyoxyethylene octylphenol ether, ethoxylated isooctylphenol, octylphenol, nonylphenol, alkylphenol polyglycol ethers, tributylphenyl polyglycol ether, tristerylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters and methylcellulose. Suitable anionic dispersants are in particular alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore arylsulfonate/formaldehyde condensates, for example condensates of sulfonated naphthalene and naphthalene derivatives with formaldehyde, condensates of naphthalene or of naphthalenesulfonic acid with phenol and formaldehyde, lignosulfonates, lignosulfite waste liquors, phosphated or sulfated derivatives of methylcellulose and polyacrylic acid salts.

Suitable for use as antifreeze agents are, in principle, all substances which lower the melting point of water. Suitable antifreeze agents include alkanols, such as methanol, ethanol, isopropanol, the butanols, glycol, glycerol, diethylene glycol and the like.

Suitable thickeners are all substances which can be used for such purposes in agrochemical compositions, for example cellulose derivatives, polyacrylic acid derivatives, xanthane, modified clays and finely divided silica.

Suitable for use as antifoams are all defoamers customary for formulating agrochemically active compounds. Particularly suitable are silicone antifoams and magnesium stearate.

Suitable for use as preservatives are all preservatives which can be employed for such purposes in agrochemical compositions. Dichlorophene, isothiazolenes, such as 1,2-benzisothiazol-3(2H)-one, 2-methyl-2H-isothiazol-3-one hydrochloride, 5-chloro-2-(4-chlorobenzyl)-3(2H)-isothiazolone, 5-chloro-2-methyl-2H-isothiazol-3-one, 5-chloro-2-methyl-2H-isothiazol-3-one, 5-chloro-2-methyl-2H-isothiazol-3-one hydrochloride, 4,5-dichloro-2-cyclohexyl-4-isothiazolin-3-one, 4,5-dichloro-2-octyl-2H-isothiazol-3-one, 2-methyl-2H-isothiazol-3-one, 2-methyl-2H-isothiazol-3-one calcium chloride complex, 2-octyl-2H-isothiazol-3-one, and benzyl alcohol hemiformal may be mentioned by way of example.

Adhesives/tackifiers may be added to improve the adhesion of the effective components on the shoots after treating. Suitable adhesives are EO/PO-based block copolymer surfactants, but also polyvinyl alcohols, polyvinyl pyrrolidones, polyacrylates, polymethacrylates, polybutenes, polyisobutenes, polystyrene, polyethyleneamines, polyethyleneamides, polyethyleneimines (Lupasol®, Polymin®), polyethers and copolymers derived from these polymers.

Suitable compositions for soil treatment include granules which may be applied in-furrow, as broadcast granules or as impregnated fertilizer granules, and also spray applications which are applied to the soil as a preemergent or postemergent spray.

Suitable compositions for treating the plants, in particular the overground parts thereof, especially the "open wounds" and the seedlings (especially the seedlings' leaves), include spray applications, dusts and microgranules, spray applications being preferred.

Formulations suitable for producing spray solutions for the direct application are:
I soluble concentrates (SL, LS)
II) dispersible concentrates (DC)
III emulsifiable concentrates (EC)
IV emulsions (EW, EO)
V suspensions (SC)
VI water-dispersible and water-soluble granules (WG)
VII water-dispersible and water-soluble powders (WP, SP)

For treating the shoots (before planting), it is possible to use some of the methods customary for treating or dressing seed, such as, but not limited to, dressing, coating, dusting, soaking, film coating or dripping the shoots with or into the active ingredient or a preparation thereof. For example, the treatment may be carried out by mixing the shoots with the particular amount desired of active ingredient formulations either as such or after prior dilution with water in an apparatus suitable for this purpose, for example a mixing apparatus for solid or solid/liquid mixing partners, until the composition is distributed uniformly on the shoots. If appropriate, this is followed by a drying operation.

The superabsorbers are generally applied to the growth medium or the field by mixing the growth medium or the soil with them or by applying the desired amount of superabsorber into the holes digged for the shoot or the seedling. The latter method is preferred for the application of superabsorbers to the field.

By the method according to the invention significantly less area is required for reproduction of the sugar cane plants as compared to traditional methods, but also with Plene®, as one adult sugar cane plant gives rise to an enhanced number of shoots. The method of the invention also reduces the risk of having non-sprouting sugar cane plants in the filed, which wastes valuable farming land. As the shoots/seedlings are protected during the sensitive first growth stages and are only transplanted to the field or exposed to ambient conditions after their rooting system is well developed, the method leads to healthy and vigorous seedlings and adult sugar cane plants growing therefrom, and especially the treatment of the seedlings with at least one strobilurin fungicide while growing contributes significantly to this.

EXAMPLES

Example 1

On an area of 0.1 hectares where sugar cane plants were growing with a distance between the rows of approximately 1.5 m, the top part of the 8 months old sugar cane plants was removed by chopping off with a machete in a height of approximately 2-2.5 m. The removed top part was discarded. After 30 days, on the below, remaining stalks, shoots ("$1^{st}$ generation") had developed from the buds. The top parts (approximately 30 cm) of these shoots were removed by cutting. New shoots ("$2^{nd}$ generation") developed from the cut shoots of the $1^{st}$ generation. 30 days after cutting the top part of the $1^{st}$ generation shoots, the $2^{nd}$ generation shoots were removed by cutting them off closely to the nodes. On average, every node had produced three $2^{nd}$ generation shoots. The removed $2^{nd}$ generation shoots were each placed in pots filled with humid coconut fibers. The pots were placed in a greenhouse, and seedlings were grown from the planted shoots at 25-35° C. and 70-80% humidity. While in the greenhouse, the shoots/seedlings were watered sufficiently. One part of the seedlings was treated once with pyraclostrobin (in form of the commercial product Comet®; EC; 250 g/l) by immersing the entire tray containing the planted shoots for 10 min into a solution containing 4 ml of Comet® concentrate per l; i.e. 1 g pyraclostrobin per l. Another part of the seedlings remained untreated (control). 30 to 45 days after having been placed in the greenhouse, the surviving seedlings were transferred to an acclimatization area and kept for 15 days. Then they were counted and transplanted to a field. In sum 96,000 seedlings had been obtained. This number was sufficient for planting an area of 6.4 hectares with the same distance between the rows and the plants in the rows as in the originating field. The seedlings which had been treated with pyraclostrobin while in the greenhouse showed a more intense, greener color and were more vigorous. 20 days after transplanting, the plant height of the treated and untreated plants was determined. The results are compiled in the table below:

TABLE

| Treatment | Concentration [g a.i./l] | Plant height [cm] |
| --- | --- | --- |
| (control) | — | 29.4 |
| pyraclostrobin | 1 | 38.3 |

As the results show, the treatment with pyraclostrobin leads to an increase in plant height of more than 30%. Moreover the young plants are in total more vigorous.

We claim:

1. A method for cultivating sugar cane, which method comprises
   (i) breaking in a living 6 to 18 months old sugar cane plant the apical dominance by cutting off the top part of the stalk so that the below stalk still comprises 5 to 15 nodes, by treating the plant or a part thereof with at least one herbicide;
   (ii) in case that the apical dominance is broken by cutting off the top part of the stalk: optionally treating a cut surface of the below stalk obtained in step (i) with at least one fungicide, at least one insecticide, at least one wound-protecting material, or at least one growth regulator;
   (iii) cutting off the top part of at least some shoots emerged from the nodes of the below stalk obtained in steps (i) or (ii) above the meristematic tissue;
   (iv) optionally treating the cut surface of the shoots obtained in step (iii) with at least one fungicide, at least one insecticide, at least one wound-protecting material, or at least one growth regulator;
   (v) optionally cutting off the top part of newly formed shoots emerged from the cut shoots obtained in steps (iii) or (iv) above the meristematic tissue;
   (vi) optionally treating the cut surface of the newly formed shoots obtained in step (v) with at least one fungicide, at least one insecticide, at least one wound-protecting material, or at least one growth regulator;
   (vii) optionally repeating step (v) and optionally also step (vi) one or several times;
   (viii) cutting off newly formed shoots emerged from the cut shoots obtained in steps (iii), (iv), (v), (vi) or (vii) when they are 10 to 60 cm long so that they comprise at least part of the meristematic tissue;
   (ix) optionally treating the newly formed shoots obtained in step (viii) with at least one fungicide, at least one insecticide, at least one nematicide, at least one wound-protecting material, or at least one growth regulator;

(x) planting the newly formed shoots of the sugar cane plant obtained in step (viii) or (ix) in a growth medium;

(xi) optionally treating the newly formed shoots obtained in step (viii) or (ix) or the growth medium before, during or shortly after planting with at least one fertilizer, at least one fungicide, at least one insecticide, at least one nematicide, at least one growth regulator, at least one superabsorber, or growth-promoting bacteria;

(xii) growing seedlings from the newly formed shoots obtained in step (viii) or (ix) at a temperature of at least 15° C.;

(xiii) treating the seedlings of step (xii), while growing, with at least one strobilurin fungicide comprising pyraclostrobin;

(xiv) 10 to 120 days after planting the newly formed shoots obtained in step (viii) or (ix) in the growth medium of step (x), if the growth medium is not a field, planting the seedlings treated with the at least one strobilurin fungicide in step (xiii) obtained from the shoots to the field, where the field has optionally been treated with at least one fertilizer, at least one fungicide, at least one insecticide, at least one nematicide, at least one growth regulator, at least one superabsorber, or growth-promoting bacteria before or during planting, or, in case the growth medium is a field, exposing the seedlings obtained from the shoots to ambient conditions; and (xv) optionally treating the seedlings of step (xii) or the field of step (xiv) during or after planting in the field or after exposing to ambient conditions with least one fungicide, at least one insecticide, at least one nematicide, at least one growth regulator, at least one superabsorber, or at least one freshness-preservation polymer.

2. The method as claimed in claim 1, where in step (i) the top part which is cut off comprises the last, top node.

3. The method as claimed in claim 1, where in step (i) the apical dominance is broken by treating the plant or a part thereof with the at least one herbicide.

4. The method as claimed in claim 3, where the herbicide is selected from the group consisting of actyl CoA carboxylase inhibitors, herbicides which interact with photosystem I electron diversion and auxin transport inhibitors.

5. The method as claimed in claim 4, where the herbicides are selected from the group consisting of clodinafop propargyl, cyhalofop butyl, diclofop methyl, fenoxaprop-P-ethyl, fluazifop-P-butyl, haloxyfop-R-methyl, propaquizafop, quizalofop-P-ethyl, alloxydim, butroxydim, clethodim, cycloxydim, profoxydim, sethoxydim, tepraloxydim, tralkoxydim, diquat, paraquat, diflufenzopyr, diflufenzopyr-sodium, naptalam and naptalam-sodium.

6. The method as claimed in claim 1, where in step (viii) the newly formed shoots are removed when they are 20 to 40 cm long.

7. The method as claimed in claim 1, where in step (x) the newly formed shoots obtained in step (viii) or (ix) are planted in a container containing the growth medium.

8. The method as claimed in claim 7, where the container is placed in a greenhouse and in step (xii) seedlings are grown from a shoot in the greenhouse.

9. The method as claimed in claim 1, where in step (x) the newly formed shoots obtained in step (viii) or (ix) are planted in the growth medium and grown under a cover foil.

10. The method as claimed in claim 1, where the seedlings are grown from the newly formed shoots obtained in step (viii) or (ix) at the temperature of from 18 to 35° C.

11. The method as claimed in claim 1, where the seedlings are grown from the newly formed shoots obtained in step (viii) or (ix) at a humidity of from 40 to 100%.

12. The method as claimed in claim 1, where the at least one strobilurin fungicide is selected from the group consisting of azoxystrobin, dimoxystrobin, enestroburin, fluoxastrobin, kresoxim-methyl, metominostrobin, orysastrobin, picoxystrobin, pyraclostrobin, pyraoxystrobin, pyrametostrobin, pyribencarb, trifloxystrobin, 2-(2-(6-(3-chloro-2-methyl-phenoxy)-5-fluoro-pyrimidin-4-yloxy)-phenyl)-2-methoxy-imino-N-methyl-acetamide, 3-methoxy-2-(2-(N-(4-methoxy-phenyl)-cyclopropane-carboximidoylsulfanylmethyl)-phenyl)-acrylic acid methyl ester, methyl (2-chloro-5-[1-(3-methylbenzyloxyimino)ethyl]benzyl)carbamate and 2-(2-(3-(2,6-dichlorophenyl)-1-methyl-allylideneaminooxymethyl)-phenyl)-2-methoxyimino-N-methyl-acetamide.

13. The method as claimed in claim 12, where the strobilurin fungicide is pyraclostrobin.

14. The method as claimed in claim 1, where the planting of the seedlings to the field is carried out using an automatic or semi-automatic planting machine.

15. The method as claimed in claim 1, where the planting of the seedlings to the field or the exposing of the seedlings to ambient conditions is carried out 25 to 80 days after planting the shoot in the growth medium.

16. The method as claimed in claim 1, where the at least one fungicide is selected from the group consisting of A) an azole, selected from the group consisting of azaconazole, bitertanol, bromuconazole, cyproconazole, difenoconazole, diniconazole, diniconazole-M, epoxiconazole, etaconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-(4-chloro-phenyl)-2-([1,2,4]triazol-1-yl)-cycloheptanol, cyazofamid, imazalil, pefurazoate, prochloraz, triflumizol, benomyl, carbendazim, fuberidazole, thiabendazole, ethaboxam, etridiazole, hymexazole and 2-(4-chloro-phenyl)-N-[4-(3,4-dimethoxy-phenyl)-isoxazol-5-yl]-2-prop-2-ynyloxy-acetamide;

B) a strobilurin, selected from the group consisting of azoxystrobin, dimoxystrobin, enestroburin, fluoxastrobin, kresoxim-methyl, meto-minostrobin, orysastrobin, picoxystrobin, pyraclostrobin, pyraoxystrobin, pyrametostrobin, pyribencarb, trifloxystrobin, 2-(2-(6-(3-chloro-2-methyl-phenoxy)-5-fluoro-pyrimidin-4-yloxy)-phenyl)-2-methoxyimino-N-methyl-acetamide, 3-methoxy-2-(2-(N-(4-methoxy-phenyl)-cyclopropane-carboximidoylsulfanylmethyl)-phenyl)-acrylic acid methyl ester, methyl (2-chloro-5-[1-(3-methylbenzyloxyimino)-ethyl]benzyl)carbamate and 2-(2-(3-(2,6-dichlorophenyl)-1-methyl-allylidene-aminooxymethyl)-phenyl)-2-methoxyimino-N-methyl-acetamide;

C) a carboxamide, selected from the group consisting of benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penthiopyrad, sedaxane, tecloftalam, thifluzamide, tiadinil, 2-amino-4-methyl-thiazole-5-carboxanilide, 2-chloro-N-(1,1,3-trimethyl-indan-4-yl)-nicotinamide, N-(3',4',5'-trifluorobiphenyl-2-yl)-3- difluoromethyl-1-methyl-1H-pyrazole-4-carboxamide (fluxapyroxade), N-(4'-trifluoromethylthiobiphenyl-2-yl)-3-difluoromethyl-1-methyl-1H-pyrazole-4-carboxamide, N-(2-(1,3-dimethyl-butyl)-phenyl)-1,3-dimethyl-5-fluoro-1H-pyrazole-4-carboxamide and N-(2-(1,3,3-trimethyl-butyl)-phenyl)-1,3-dimethyl-5-fluoro-1H-pyrazole-4-carboxamide, dimethomorph, flumorph, pyrimorph, flumetover, fluopicolide, fluopyram, zoxamide, N-(3-ethyl-3,5,5-trimethyl-cyclohexyl)-3-formylamino-2-hydroxy-benzamide, carpropamid, dicyclomet, mandiproamid, oxytetracyclin, silthiofam and N-(6-methoxy-pyridin-3-yl) cyclopropanecarboxylic acid amide;

D) a heterocyclic compound, selected from the group consisting of
fluazinam, pyrifenox, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine, 2,3,5,6-tetra-chloro-4-methanesulfonyl-pyridine, 3,4,5-trichloropyridine-2,6-di-carbonitrile, N-(1-(5-bromo-3-chloro-pyridin-2-yl)-ethyl)-2,4-dichloronicotinamide, N-[(5-bromo-3-chloro-pyridin-2-yl)-methyl]-2,4-dichloro-nicotinamide, bupirimate, cyprodinil, diflumetorim, fenarimol, ferimzone, mepanipyrim, nitrapyrin, nuarimol, pyrimethanil, triforine, fenpiclonil, fludioxonil, aldimorph, dodemorph, dodemorph-acetate, fenpropimorph, tridemorph, fenpropidin, fluoroimid, iprodione, chlozolinate, procymidone, vinclozolin, famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester, acibenzolar-S-methyl, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole, 5-chloro-7-(4-methylpiperidin-1-yl)-6-(2,4,6-trifluorophenyl)-[1,2,4]triazolo[1,5-a]pyrimidine and 5-ethyl-6-octyl-[1,2,4]triazolo[1,5-a]pyrimidine-7-ylamine;

E) a carbamate, selected from the group consisting of
ferbam, mancozeb, maneb, metam, methasulphocarb, metiram, propineb, thiram, zineb, ziram, benthiavalicarb, pyributicarb, diethofencarb, iprovalicarb, iodocarb, propamocarb, propamocarb hydrochlorid, prothiocarb, valiphenal and N-(1-(1-(4-cyano-phenyl)ethanesulfonyl)-but-2-yl) carbamic acid-(4-fluorophenyl) ester;

F) another active compound, selected from the group consisting of
a guanidines selected from the group consisting of: guanidine, dodine, dodine free base, guazatine, guazatine-acetate, iminoctadine, iminoctadine-triacetate, and iminoctadine-tris(albesilate);
an antibiotic selected from the group consisting of: kasugamycin, kasugamycin hydrochloride-hydrate, streptomycin, polyoxine, and validamycin A;
a nitrophenyl derivate selected from the group consisting of: binapacryl, dinobuton, dinocap, meptyldinocap, nitrthal-isopropyl, and tecnazen,
organometal compounds: fentin salts;
a sulfur-containing heterocyclyl compound selected from the group consisting of: dithianon, isoprothiolane;

an organophosphorus compound selected from the group consisting of: edifenphos, fosetyl, fosetyl-aluminum, iprobenfos, phosphorous acid and its salts, pyrazophos, and tolclofos-methyl;
an organochlorine compound selected from the group consisting of: chlorothalonil, dichlofluanid, dichlorophen, flusulfamide, hexachlorobenzene, pencycuron, pentachlorphenole and its salts, phthalide, quintozene, thiophanate-methyl, tolylfluanid, and N-(4-chloro-2-nitro-phenyl)-N-ethyl-4-methyl-benzenesulfonamide;
an inorganic active substance selected from the group consisting of: Bordeaux mixture, copper acetate, copper hydroxide, copper oxychloride, basic copper sulfate, and sulfur;
another active compound selected from the group consisting of: biphenyl, bronopol, chloroneb, cyflufenamid, cymoxanil, dicloran, tecnazene, diphenylamin, metrafenone, mildiomycin, oxin-copper, prohexadione-calcium, spiroxamine, tolylfluanid, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, acetic acid 6-tert.-butyl-8-fluoro-2,3-dimethyl-quinolin-4-yl ester and methoxy-acetic acid 6-tert-butyl-8-fluoro-2,3-dimethyl-quinolin-4-yl ester; and G) a biological control agent having fungicidal activity.

17. The method as claimed in claim 16, where the biological control agents are selected from non-pathogenic bacteria selected from the group consisting of *Pseudomonas fluorescens, Pseudomonas putida, Streptomyces griseus, Streptomyces ochraceisleroticus, Streptomyces graminofaciens, Streptomyces corchousii, Streptomyces spiroverticillatus, Streptomyces griseovirdis, Streptomyces hygroscopicus, Bacillus subtilis, Bacillus cereus, Bacillus mycoides, Bacillus pumilus, Bacillus licheniformis, Bacillus thuringensis*, and metabolites produced from said bacteria; non-pathogenic fungi selected from the group consisting of *Trichoderma* spp., *Trichoderma harzianum, Trichoderma viridae, Verticillium lecanii, Sporidesmium sclerotiorum* and Zygomycetes, and metabolites produced from said fungi; resin acids, plant extracts of *Reynoutria sachalinensis*; and plant defence induction agents.

18. The method as claimed in claim 15, where the at least one fungicide is selected from the group consisting of cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, cyazofamid, benomyl, carbendazim, ethaboxam, azoxystrobin, dimoxystrobin, fluoxastrobin, fluxapyroxade, kresoxim-methyl, orysastrobin, picoxystrobin, pyraclostrobin, trifloxystrobin, bixafen, boscalid, sedaxane, fenhexamid, metalaxyl, isopyrazam, mefenoxam, ofurace, dimethomorph, flumorph, fluopicolid (picobenzamid), zoxamide, carpropamid, mandipropamid, fluazinam, cyprodinil, fenarimol, mepanipyrim, pyrimethanil, triforine, fludioxonil, dodemorph, fenpropimorph, tridemorph, fenpropidin, iprodione, vinclozolin, famoxadone, fenamidone, probenazole, proquinazid, acibenzolar-S-methyl, captafol, folpet, fenoxanil, quinoxyfen, 5-ethyl-6-octyl-[1,2,4]triazolo[1,5-a]pyrimidine-7-ylamine, mancozeb, metiram, propineb, thiram, iprovalicarb, flubenthiavalicarb (benthiavalicarb), propamocarb, dithianon, fentin salts, fosetyl, fosetyl-aluminium, $H_3PO_3$ and salts thereof, chlorthalonil, dichlofluanid, thiophanat-methyl, copper acetate, copper hydroxide, copper oxychloride, copper sulfate, sulfur, cymoxanil, metrafenone, spiroxamine and *Bacillus subtilis* and its metabolites.

19. The method as claimed in claim 18, where the at least one fungicide is selected from azoxystrobin, dimoxystrobin, fluoxastrobin, fluxapyroxade, kresoxim-methyl, orysastrobin, picoxystrobin, pyraclostrobin, trifloxystrobin and *Bacillus subtilis* and its metabolites.

20. The method as claimed in claim 1, where the at least one insecticide is selected from the group consisting of
    a) a pyrethroid compound selected from the group consisting of acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin and transfluthrin;
    b) a nicotinic receptor agonist/antagonist compound selected from the group consisting of acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022;
    c) a GABA gated chloride channel antagonist compound selected from the group consisting of chlordane, endosulfan, gamma-HCH (lindane); ethiprole, fipronil, pyrafluprole, and pyriprole;
    d) a chloride channel activator selected from the group consisting of abamectin, emamectin benzoate, milbemectin and lepimectin; and
    e) an inhibitors of chitin biosynthesis:
        e1) selected from the group consisting of benzoyl ureas: bistrifluron, chlorfluazuron, diflubenzuron, flucycloxuron, flufenoxuron, hexaflumuron, lufenuron, novaluron, noviflumuron, teflubenzuron, and triflumuron.

21. The method as claimed in claim 20, where the at least one insecticide is selected from the group consisting of fipronil, acetamiprid, chlothianidin, imidacloprid, thiamethoxam, teflubenzuron and abamectin.

22. The method as claimed in claim 1, where the at least one nematicide is selected from the group consisting of
    an antibiotic nematicide;
    a botanical nematicide;
    an extract of *Quillaja* or *Gleditsia;*
    a saponine;
    a carbamate nematicide selected from the group consisting of benomyl, carbofuran, carbosulfan and cloethocarb;
    an oxime carbamate nematicide selected from the group consisting of alanycarb, aldicarb, aldoxycarb, oxamyl and tirpate;
    a fumigant nematicide selected from the group consisting of dithioether and methyl bromide;
    an organophosphorus nematicide selected from the group consisting of:
        an organophosphate nematicide selected from the group consisting of diamidafos; fenamiphos; fosthietan and phosphamidon;
        an organothiophosphate nematicide selected from the group consisting of cadusafos, chlorpyrifos, dichlofenthion, dimethoate, ethoprophos, fensulfothion, fosthiazate, heterophos, isamidofos, isazofos, phorate, phosphocarb, terbufos, thionazin and triazophos;
        a phosphonothioate nematicide selected from the group consisting of imicyafos and mecarphon; and
    an unclassified nematicide selected from the group consisting of acetoprole, benclothiaz, chloropicrin, dazomet, DBCP, DCIP, 1,2-dichloropropane, 1,3-dichloropropene, fluensulfone, furfural, metam, methyl iodide, methyl isothiocyanate and xylenols.

23. The method as claimed in claim 1, where the growth-promoting bacteria are selected from the group consisting of bacteria of the genera *azospirillum, azotobacter, azomonas, bacillus, beijerinckia, burkholderia, clostridium, cyanobacteria, enterobacter, erwinia, gluconobacter, klebsiella* and *streptomyces.*

24. The method as claimed in claim 23, where growth-promoting bacteria are selected from the group consisting of *Azospirillum amazonense, Herbaspirillum seropedicae, Herbaspirillum rubrisubalbicans, Burkholderia tropica, Gluconacetobacter diazotrophicus, Pseudomonas fluorescens, Pseudomonas putida. Streptomyces griseus, Streptomyces ochraceisleroticus, Streptomyces graminofaciens, Streptomyces corchousii, Streptomyces spiroverticillatus, Streptomyces griseovirdis, Streptomyces hygroscopicus, Bacillus subtilis, Bacillus cereus, Bacillus mycoides, Bacillus pumilus, Bacillus licheniformis* and *Bacillus thuringensis.*

25. The method as claimed in claim 1, where the at least one growth regulator is selected from the group consisting of acylcyclohexanediones, mepiquat chloride and chlormequatchloride selected from the group consisting of prohexadione, prohexaione-Ca, trinexapac, trinexapac-ethyl, mepiquat chloride and chlormequatchloride.

26. The method as claimed in claim 1, where comprising at least one rooting enabler is selected from the group consisting of strobilurin fungicides, nicotinic receptor agonists/antagonists, auxins, gibberellins, gibberellic acid, cytokinins, humic acids, extracts of *Quillaja* or *Gleditsia,* saponines, biological control agents and plant defence induction agents.

27. The method as claimed in claim 1, where the at least one wound-protecting material is selected from the group consisting of non-toxic inorganic and organic film-forming or coating polymers.

28. The method as claimed in claim 27, where the wound-protecting material is selected from the group consisting of superabsorbers, superabsorber-treated polymers, aliphatic-aromatic copolyesters, freshness-preservation polymers, waxes, soluble glass and Tingui seed coat preparations.

* * * * *